United States Patent
Masumura

(10) Patent No.: US 8,364,414 B2
(45) Date of Patent: Jan. 29, 2013

(54) APPARATUS AND METHOD FOR PROCESSING BIOLOGICAL INFORMATION

(75) Inventor: Takahiro Masumura, Tucson, AZ (US)

(73) Assignee: Canon Kabushiki Kaisha, Tokyo (JP)

( * ) Notice: Subject to any disclaimer, the term of this patent is extended or adjusted under 35 U.S.C. 154(b) by 627 days.

(21) Appl. No.: 12/572,486

(22) Filed: Oct. 2, 2009

(65) Prior Publication Data

US 2010/0094561 A1     Apr. 15, 2010

(30) Foreign Application Priority Data

Oct. 3, 2008   (JP) ................. 2008-258570

(51) Int. Cl.
*G06F 19/00*    (2006.01)

(52) U.S. Cl. ............ 702/19; 702/127; 73/632; 356/432; 600/476

(58) Field of Classification Search .................... 356/432
See application file for complete search history.

(56) References Cited

U.S. PATENT DOCUMENTS

| | | | |
|---|---|---|---|
| 5,840,023 A | 11/1998 | Oraevsky | |
| 6,957,096 B2 | 10/2005 | Sfez | |
| 2009/0069674 A1* | 3/2009 | Masumura et al. | 600/425 |

OTHER PUBLICATIONS

Minghua Xu, Lihong V. Wang, Photoacoustic imaging in biomedicine, Review of Scientific Instruments 77, 041101, 2006.

* cited by examiner

*Primary Examiner* — Jonathan C Teixeira Moffat
*Assistant Examiner* — Hien Vo
(74) *Attorney, Agent, or Firm* — Canon U.S.A., Inc. IP Division

(57) ABSTRACT

A biological information processing apparatus includes the following elements. A light source irradiates biological tissue with light. A transducer functions as an ultrasonic wave transmitting unit that applies an ultrasonic wave to a local region in the biological tissue. A photodetector detects modulated light obtained by modulating the light from the light source with the ultrasonic wave in the local region. The transducer also functions as an acoustic wave detecting unit that detects an acoustic wave emitted from the local region at a time when the local region absorbs the light from the light source. An absorption characteristic in the local region is calculated using an acoustic signal, serving as an output of the acoustic wave detecting unit, on the basis of a light intensity in the local region calculated based on a modulation signal, serving as an output of the photodetector.

13 Claims, 8 Drawing Sheets

APPARATUS AND METHOD FOR PROCESSING BIOLOGICAL INFORMATION

BACKGROUND OF THE INVENTION

1. Field of the Invention

The present invention relates to an apparatus and method for processing biological information.

2. Description of the Related Art

Research on optical imaging apparatuses for irradiating biological tissue with light emitted from a light source such as a laser, and imaging biological information obtained on the basis of incident light is being advanced actively in the medical field.

One of optical imaging techniques is photoacoustic tomography (PAT) called photoacoustic imaging. The photoacoustic imaging is a method of obtaining a distribution of optical characteristic values in biological tissue using the properties of an ultrasonic wave that is scattered in vivo less than light (refer to U.S. Pat. No. 5,840,023 and M, Xu, L. V. Wang, "photoacoustic imaging in biomedicine", Review of scientific instruments, 77, 041101, 2006 (hereinafter, referred to as "Non-patent Document 1").

According to the method, biological tissue is irradiated with pulsed light generated from a light source to detect an acoustic wave generated from biological tissue which has absorbed the energy of the pulsed light propagated and diffused inside the biological tissue. Specifically, using the difference between the absorptance of optical energy of a region of interest, such as a tumor, and that of another tissue, a transducer receives an elastic wave generated from the region of interest when the region momentarily expands by absorbing the energy of applied light. Detected signals are analyzed, thus obtaining a distribution of optical characteristic values in the biological tissue, especially, a distribution of optical energy absorption densities (hereinafter, referred to as "optical energy absorption density distribution").

One of such optical imaging techniques other than the PAT is diffuse optical tomography (DOT) called diffuse optical imaging. The diffuse optical imaging is a technique of irradiating biological tissue with light emitted from a light source, detecting weak light propagated and diffused in the biological tissue through a high-sensitive photodetector, and imaging a distribution of optical characteristic values in the biological tissue on the basis of detected signals.

Furthermore, one of imaging techniques using light and an ultrasonic wave is acousto-optical tomography (AOT). The AOT is a technique of irradiating biological tissue with light, applying a focused ultrasonic wave to a local region in the biological tissue, and detecting modulated light through a photodetector using such an effect (acousto-optic effect) that the light is modulated by the ultrasonic wave (refer to U.S. Pat. No. 6,957,096). It is known that the AOT and the PAT yield higher resolution than the DOT because these techniques each detect a signal of a local region where light and an ultrasonic wave interact with each other.

According to the PAT, an acoustic wave absorbed and generated in a local region of interest is measured, thus obtaining local optical absorption information. A pressure p of the acoustic wave generated in the region of interest is expressed using a distance z between the region and a light irradiation point by the following expression:

$$P(z) = \Gamma \mu_a(z) \Phi(z) \tag{1}$$

where $\Gamma$ denotes a Gruneisen coefficient (thermal-to-acoustic conversion efficiency), $\mu_a(z)$ denotes an absorption coefficient at a position in the distance z, and $\Phi(z)$ denotes the intensity of light (hereinafter, referred to as "light intensity") at the position in the distance z. The Gruneisen coefficient $\Gamma$, serving as an elastic characteristic value, is obtained by dividing the product of an isobaric volume expansion coefficient $\beta$ and a squared sound speed c by a specific heat Cp.

It is known that $\Gamma$ takes a substantially constant value so long as a biological tissue is determined. Accordingly, a change in sound pressure P, indicating the magnitude of the acoustic wave, is measured in a time-resolved manner, thereby obtaining the product of $\mu_a$ and $\Phi$, namely, an optical energy absorption density distribution H (refer to Non-patent Document 1).

To accurately image a distribution of absorption coefficients $\mu_a(z)$ in biological tissue on the basis of the sound pressure P as a measured value, the light intensity $\Phi(z)$ at the position z of the region of interest has to be estimated accurately, as will be understood from Expression (1).

According to the technique disclosed in Non-patent Document 1, as an approach to estimation of the light intensity $\Phi(z)$, an average light attenuation coefficient $\Phi_{eff}(\gamma)$ in biological tissue is used and the Lambert-Beer Law and the diffusion theory are used to obtain the light intensity $\Phi(z)$. Using the light intensity $\Phi(z)$, the absorption coefficient $\mu_a(z)$ is obtained based on the sound pressure P(z). The attenuation coefficient $\mu_{eff}(\gamma)$ is expressed by the following expression.

$$\mu_{eff} = \sqrt{3\mu_a(\mu'_s + \mu_a)} \tag{2}$$

In Expression (2), $\mu'_s$ denotes an equivalent scattering coefficient. When a specimen is optically homogeneous, Expression (2) can be used. If the specimen is heterogeneous optically, however, it is difficult to accurately estimate the light intensity $\Phi(z)$. For example, the specimen is irradiated with light and diffused light radiated from the specimen is measured, so that the attenuation coefficient $\mu_{eff}(\gamma)$ can be estimated. The attenuation coefficient $\mu_{eff}(\gamma)$ is seriously affected by the optical characteristics of part in the vicinity of the surface of the specimen. In addition, the intensity of light which has reached a region of interest relatively deeper than the surface is affected by the optical characteristics of heterogeneous tissues between the surface and the region. Unfortunately, the light intensity $\Phi(z)$ of the region of interest is extremely shifted from the light intensity estimated using the attenuation coefficient $\mu_{eff}(\gamma)$. If the light intensity $\Phi(z)$ is not estimated accurately, the absorption coefficient $\mu_a(z)$ of the region of interest is not obtained with high accuracy.

SUMMARY OF THE INVENTION

The present invention provides a biological information processing apparatus and method capable of accurately estimating a light intensity in a local region of interest with high accuracy, thus allowing for high accuracy estimation of an absorption coefficient based on an acoustic signal of the PAT.

According to an aspect of the present invention, a biological information processing apparatus includes a light source configured to irradiate biological tissue with light, an ultrasonic wave transmitting unit configured to apply an ultrasonic wave to a local region in the biological tissue, a photodetecting unit configured to detect modulated light obtained by modulating the light from the light source with the ultrasonic wave in the local region, an acoustic wave detecting unit configured to detect an acoustic wave emitted from the local region at a time when the local region absorbs the light from the light source, and an arithmetic logical unit configured to calculate an absorption characteristic in the local region using an acoustic signal, serving as an output of the acoustic wave detecting unit, on the basis of a light intensity in the local region calculated based on a modulation signal, serving as an output of the photodetecting unit.

According to another aspect of the present invention, there is provided a method for processing biological information. The method includes the steps of, when a local region in biological tissue is irradiated with light and is simultaneously irradiated with an ultrasonic wave, detecting modulated light obtained by modulating the light with the ultrasonic wave in the local region, detecting an acoustic wave emitted from the local region at a time when the local region absorbs the light, and calculating an absorption characteristic in the local region using an acoustic signal, obtained from the acoustic wave, on the basis of a light intensity in the local region calculated based on a modulation signal obtained from the modulated light.

According to the biological information processing apparatus and method of the present invention, a light intensity in a local region of interest is estimated accurately using the AOT technique, so that an absorption coefficient can be estimated with high accuracy using an acoustic signal of PAT. Thus, a distribution of absorption coefficients in biological tissue can be imaged with high resolution.

Other features of the present invention will be apparent from the following description taken in conjunction with the accompanying drawings, in which like reference characters designate the same or similar parts throughout the figures thereof.

DESCRIPTION OF THE EMBODIMENTS

Figure 1:
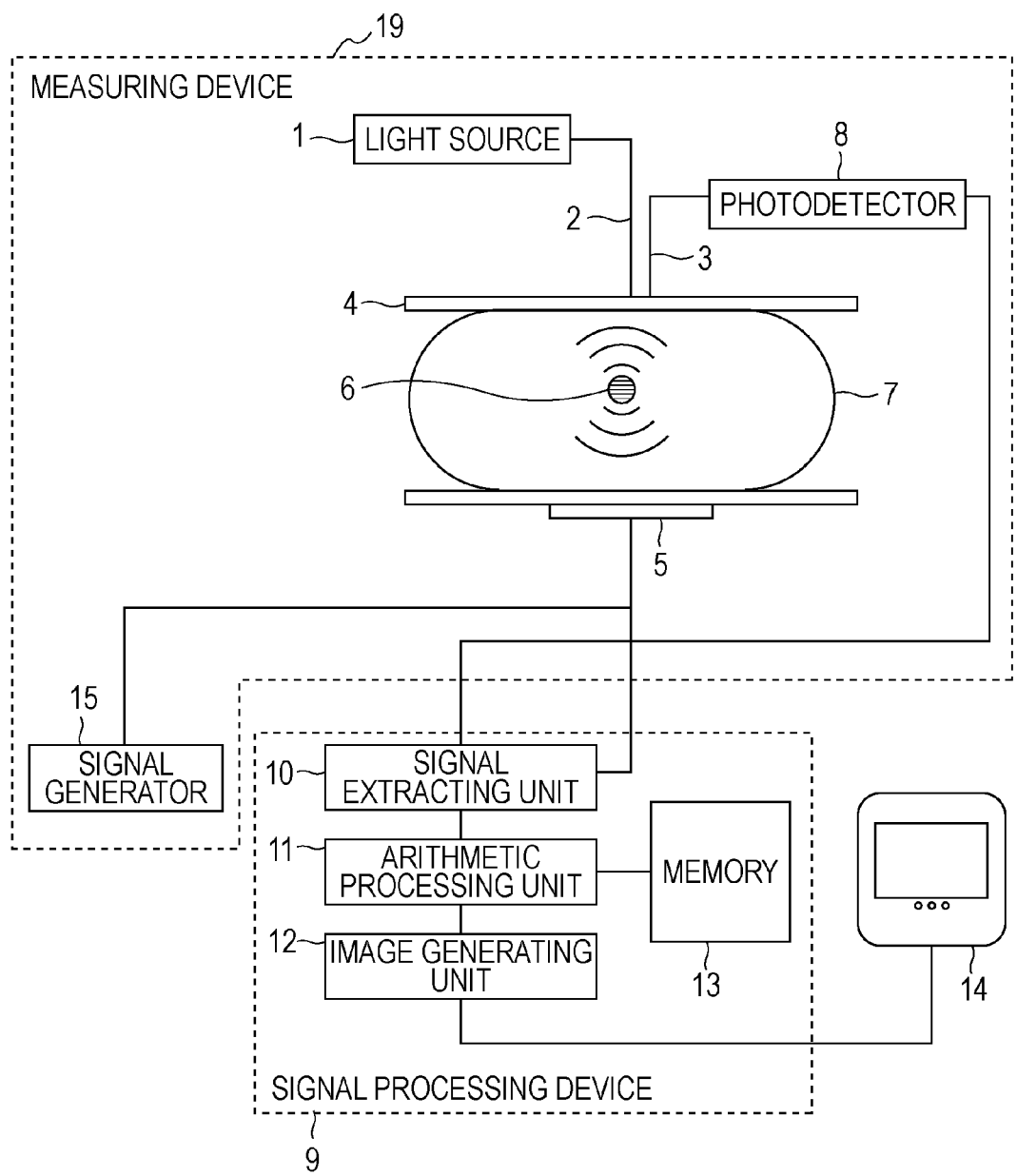
FIG. 1 is a schematic diagram illustrating an exemplary configuration of a biological information processing apparatus according to a first embodiment of the present invention.

Exemplary embodiments of the present invention will now be described in detail in accordance with the accompanying drawings. The same components are fundamentally designated by the same reference numerals and redundant description is avoided.

A biological information processing apparatus according to an embodiment of the present invention calculates an absorption characteristic in a local region using an acoustic signal obtained in photoacoustic tomography (PAT) on the basis of a light intensity in the local region calculated in acousto-optical tomography (AOT).

In the PAT, as will be understood from the foregoing Expression (1), in order to obtain a distribution of absorption coefficients ($\mu_a$) in biological tissue by measuring a change in sound pressure (P), a distribution of amounts ($\Phi$) of light applied to the biological tissue (absorber) has to be obtained in some way.

In practical intricate biological tissue, it is difficult to estimate an amount of light (hereinafter, "light amount") applied to the absorber. Unfortunately, typical sound pressure measurement using an acoustic wave allows for imaging of an optical energy absorption density distribution ($\mu_a \cdot \Phi$) alone. In other words, it is difficult to calculate the distribution of light amounts ($\Phi$) applied to the absorber on the basis of measurement of only the acoustic wave, separate the distribution of absorption coefficients ($\mu_a$) in the biological tissue from the optical energy absorption density distribution ($\mu_a \cdot \Phi$), and image the distribution of absorption coefficients ($\mu_a$). Accordingly, the distribution of accurate absorption coefficients ($\mu_a$) cannot be obtained only using the PAT. Disadvantageously, it is difficult to specify elements of biological tissue such as oxyhemoglobin or deoxyhemoglobin and measure the concentration of each element.

Absorption coefficients can be obtained by the PAT using data (hereinafter, referred to as "light amount data") indicating a light amount ($\Phi$) obtained by the AOT. As will be described in detail below, a distribution of light amounts ($\Phi$), which cannot be directly measured by the PAT, can be determined more accurately. When the light amounts ($\Phi$) obtained by the AOT and the optical energy absorption density coefficient ($\mu_a \cdot \Phi$) obtained by the PAT are used, therefore, the distribution of absorption coefficients can be quantitatively obtained with high resolution. As described above, the combination of the AOT and the PAT can improve the quantitativeness of the absorption coefficient distribution and the resolution.

A biological information processing apparatus and method according to a first embodiment of the present invention will be described below. FIG. 1 is a schematic diagram illustrating en exemplary configuration of the biological information processing apparatus according to the present embodiment.

The biological information processing apparatus according to the present embodiment includes a measuring device 19 and a signal processing device 9. The measuring device 19 is capable of measuring information in tissue of a specimen 7, serving as biological tissue, using both of the AOT and the PAT. The signal processing device 9 functions as an arithmetic logical unit configured to process various signals obtained by the measuring device 19. The biological information processing apparatus may further include a display device 14 that displays an image obtained by imaging biological information derived by signal processing.

The measuring device 19 includes the following elements mainly. A light source 1 irradiates the specimen 7, serving as biological tissue, with light. An ultrasonic transducer 5 functions as an ultrasonic transmitting unit configured to apply an ultrasonic wave to a local region (ultrasonic focused region 6) in the specimen 7. A photodetector 8 functions as a photodetecting unit configured to detect modulated light obtained by modulating the light from the light source 1 with the ultrasonic wave in the ultrasonic focused region 6. The ultrasonic transducer 5 also functions as an acoustic wave detecting unit configured to detect an acoustic wave generated from the local region irradiated with the light from the light source 1. In other words, such a single elastic wave transducer performs both of transmission of a focused ultrasonic wave in the AOT and reception of an acoustic wave in the PAT. The measuring device 19 further includes a signal generator 15 that generates a signal of, for example, a sine wave, an incidence optical fiber 2, a detection optical fiber 3, and a pair of specimen fixing plates 4.

The light source 1 is used in AOT measurement and is also used in PAT measurement. The ultrasonic transducer 5 transmits an ultrasonic wave in the AOT measurement and receives an acoustic wave in the PAT measurement. The photodetector 8 detects modulated light in the AOT measurement.

In the signal processing device 9 which functions as the arithmetic logical unit, an absorption characteristic in the local region is calculated using an acoustic signal, serving as an output of the ultrasonic transducer 5 in the PAT measurement, on the basis of a light intensity in the ultrasonic focused region 6, the light intensity being calculated using modulated light as an output of the photodetector 8 in the AOT measurement.

The specimen 7, including biological tissue of, for example, a breast, is an absorptive scatterer. The specimen 7 is fixed by the specimen fixing plates 4 while being slightly pressed in two directions. The specimen fixing plates 4 are made of an optically transparent material having an acoustic impedance relatively close to that of the specimen 7.

It is preferable that the light source 1 switch therein between continuous wave (CW) light having a long coherence length (of, for example, 1 m or more) and a constant intensity and pulsed light of several nanoseconds. The light source 1 can select a plurality of wavelengths corresponding to absorption spectra of water, fat, protein, oxyhemoglobin, and deoxyhemoglobin constituting the biological tissue. For example, wavelengths ranging of 600 to 1500 nm are appropriate, because light having such a wavelength band is absorbed poorly by water as a main element of the biological tissue and can therefore penetrate the tissue, and this wavelength band is characteristic of the spectra of fat, oxyhemoglobin, and deoxyhemoglobin. As a concrete example, the light source 1 may include a semiconductor or tunable laser generating different wavelengths. The "light source" in this specification may include two light sources, one light source generating pulsed light for the PAT measurement, the other light source generating CW light for the AOT measurement. Alternatively, a single light source capable of generating pulsed light and CW light may be used. A laser is preferably used as a light source. Instead of a laser, a light emitting diode may be used. Various lasers, such as a solid laser, a gas laser, a dye laser, and a semiconductor laser, are available.

The optical fiber 2 guides light emitted from the light source 1 to the specimen 7. A focusing optical system for efficiently guiding light from the light source 1 to one end of the optical fiber 2 may be disposed upstream of the optical fiber 2. The light incident on the specimen 7 propagates through the specimen 7 while being repeatedly absorbed and scattered.

AOT Measurement

The AOT measurement will now be described. The ultrasonic transducer 5 transmits a focused ultrasonic wave to any position (the ultrasonic focused region 6) inside the specimen 7. The frequency band of the ultrasonic wave substantially ranges from approximately 1 to tens of megahertz. The intensity of an ultrasonic wave to be applied is adjusted to an intensity range up to a safety standard level at which the ultrasonic wave can be applied safely to biological tissue.

The ultrasonic transducer 5 includes, for example, a linear array probe. An ultrasonic focused region 6 may be generated at any position in the specimen 7 by electronic focusing the array probe. Alternatively, the ultrasonic focused region 6 may be provided at any position by mechanically scanning the ultrasonic transducer 5 including a circular concave ultrasonic transducer or a transducer including an acoustic lens. As such an elastic wave transducer, a transducer using a piezoelectric phenomenon, a transducer using resonance of light, or a transducer using a change in capacity is available.

In the ultrasonic focused region (probe region) 6, a sound field according to the frequency and amplitude of an ultrasonic wave set by the ultrasonic transducer 5 is generated. In this region, a change in density of a medium is caused by sound pressure, thus resulting in a change in index of refraction (refractive index) of the medium or the displacement of a scatterer. When light emitted from the light source 1 enters the region, the phase of the light is modulated with the frequency of the ultrasonic wave by the change in refractive index of the medium or the displacement of the scatterer. In this specification, such a phenomenon is called an acousto-optic effect. In addition, the term "modulated light" means light modulated by such an acousto-optic effect caused due to an ultrasonic wave focused in a local region.

The photodetector 8 detects modulated light obtained by the acousto-optic effect in the ultrasonic focused region 6, unmodulated light that is not modulated in the ultrasonic focused region 6, and unmodulated light passed through part other than the ultrasonic focused region 6 through the optical fiber 3. As for the photodetector 8, a single sensor, such as a photomultiplier tube (PMT) or an avalanche photodiode (APD), is preferably used. Alternatively, a multi-sensor, such as a CCD or a CMOS, may be used.

The signal processing device 9 performs analysis of signals supplied from the photodetector 8 and the ultrasonic transducer 5, analysis of information related to absorption characteristics in the specimen 7, and imaging. The signal processing device 9 includes a signal extracting unit 10, an arithmetic processing unit 11, an image generating unit 12, and a memory 13.

In measurement of modulated light, the signal extracting unit 10, functioning as a filter, separates detected light into modulated light and unmodulated light. As for the signal extracting unit 10, a band bass filter that selectively detects a signal having a specific frequency or a lock-in amplifier that amplifies and detects light having a specific frequency is available. The signal extracting unit 10 obtains the intensity of modulated light from light detected by the photodetector 8.

In this specification, the term "modulation signal" means an electrical signal obtained by converting ultrasonically modulated light due to a photoelectric effect by the photodetector 8. Preferably, the electrical signal is an electrical signal including an AC component.

PAT Measurement

The PAT measurement will now be described. The specimen 7 is irradiated with pulsed light of several nanoseconds emitted from the light source 1. The energy of the light absorbed in the probe region 6 locally causes an increase in temperature, thus resulting in expansion of the volume of this region. An acoustic wave generated upon volume expansion is detected. To measure the acoustic wave from the same probe region 6 as that used in the AOT measurement, setting of electronic focusing used for transmission in the AOT measurement is used for reception. In the case of mechanical scanning with the circular concave ultrasonic transducer or the transducer including the acoustic lens, the transducer may be disposed in the same geometry as that in the AOT measurement. The signal extracting unit 10 measures the intensity of an acoustic signal obtained from the probe region 6.

In this specification, the term "acoustic wave" means an elastic wave generated from the probe region 6 by a photoacoustic effect. The term "acoustic signal" means an electrical signal obtained by converting the elastic wave generated from the probe region 6 through the ultrasonic transducer 5.

Structures of Other Components

The incidence optical fiber 2 and the detection optical fiber 3 are capable of two-dimensionally scanning the surface of one of the specimen fixing plates 4 synchronously with each other. The ultrasonic transducer 5 is controlled in accordance with the positions of the incidence optical fiber 2 and the detection optical fiber 3 to set the probe region 6. The probe region 6 is scanned relative to the specimen 7 so as to be subjected to the AOT measurement and the PAT measurement, thus obtaining a spatial measurement distribution in the specimen 7. To obtain spectral characteristics in the specimen 7, the above-described measurements may be performed while a wavelength of the light source 1 is being switched to another wavelength.

The arithmetic processing unit 11 performs signal processing, which will be described later, using a modulation signal obtained in the AOT measurement and an acoustic signal obtained in the PAT measurement. Alternatively, the arithmetic processing unit 11 calculates the concentration of each element of the specimen 7 and the proportion of the elements on the basis of spectral characteristics obtained using a plurality of wavelengths. All of the resultant data items related to the spectral characteristics are associated with data items indicating the coordinates of positions of the probe regions 6 to generate distribution data indicating a distribution of the spectral characteristics in the specimen 7.

The image generating unit 12 generates a three-dimensional tomogram (image) of the specimen 7 on the basis of the distribution data related to the spectral characteristics in the specimen 7 generated by the arithmetic processing unit 11.

The memory 13 stores signal values of the AOT measurements and the PAT measurements obtained by the signal extracting unit 10, the data generated by the arithmetic processing unit 11, and the image based on the spectral characteristics generated by the image generating unit 12. As for the memory 13, a data recording device, such as an optical disk, a magnetic disk, a semiconductor memory, or a hard disk, may be used.

The display device 14 displays an image generated by the signal processing device 9. As for the display device 14, a liquid crystal display, a CRT, or an organic electroluminescent (EL) display may be used.

Method for Processing Biological Information

An arithmetic processing method, performed by the arithmetic processing unit 11, for obtaining an absorption characteristic in the probe region 6 on the basis of an acoustic signal in the PAT measurement using a modulation signal in the AOT measurement will now be described.

Figure 2:
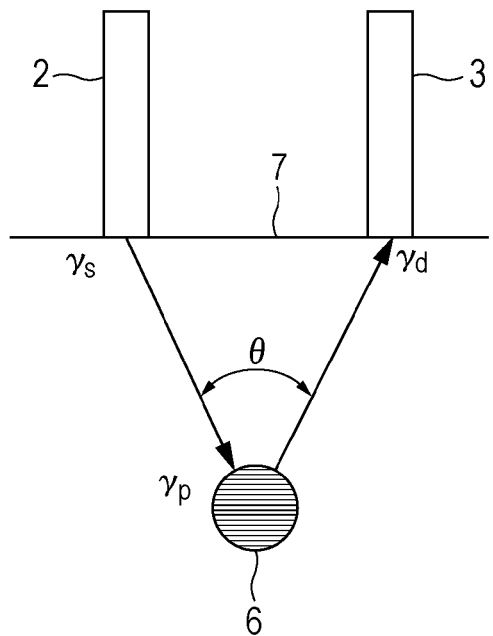
FIG. 2 is a schematic diagram illustrating an example of the positional relation among a light incident position, a light detection position, and a probe region.

Under AOT measurement conditions as shown in FIG. 2, the intensity $I_{AC}(\gamma_p)$ of modulated light which has been modulated in the probe region 6 in a position $\gamma_p$ inside the specimen 7 and has been detected can be expressed by the following expression, as described in U.S. Pat. No. 6,957,096.

$$I_{AC}(\gamma_p) = S_O \Psi(\gamma_s, \gamma_p) \eta \Psi(\gamma_p, \gamma_d) \quad (3)$$

where $\Psi(\gamma_s, \gamma_p)$ denotes a transfer function of the light intensity from a light incident position $\gamma_s$ up to the position $\gamma_p$ of the probe region 6 in the specimen 7, $\Psi(\gamma_p, \gamma_d)$ denotes a transfer function of the light intensity from the position $\gamma_p$ up to a light detection position $\gamma_d$, $S_O$ indicates the light intensity of light incident on the specimen 7, and $\eta$ indicates an efficiency at which light is modulated in the probe region 6. The transfer function $\Psi$ of the light intensity inside the specimen 7 can be modeled by a light diffusion equation, a transport equation, or a Monte Carlo simulation.

In this specification, a path through which light outgoing from the incidence optical fiber 2 is scattered and propagated up to the probe region 6 inside the specimen 7 is called an incident light propagation area. Whereas, a path through which light modulated in the probe region 6 is scattered and propagated up to the detection optical fiber 3 is called a detection light propagation area.

Figure 3:
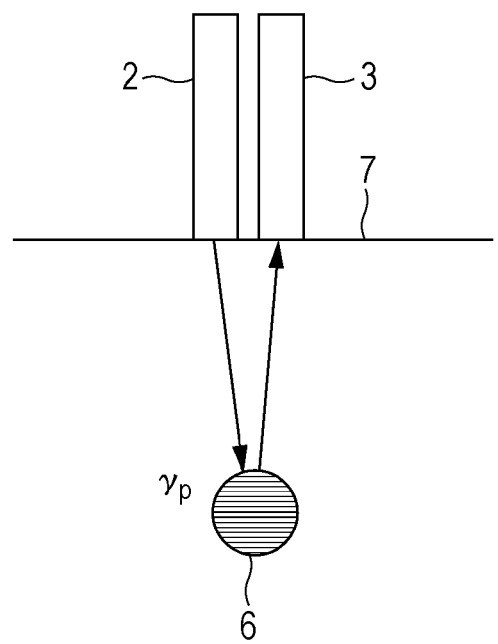
FIG. 3 is a schematic diagram illustrating another example of the positional relation among the light incident position, the light detection position, and the probe region.

As shown in FIG. 3, when the incidence optical fiber 2 and the detection optical fiber 3 are arranged such that the optical fibers are closed to each other ($\gamma_s \approx \gamma_p$), Expression (3) is expressed as follows.

$$I_{AC}(\gamma_p) = S_O \Psi(\gamma_s, \gamma_p)^2 \eta \quad (4)$$

Figure 4:
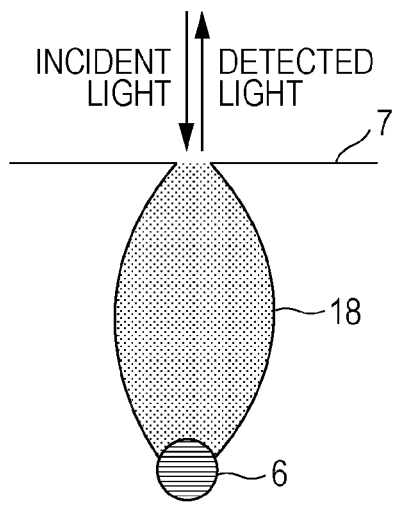
FIG. 4 is a schematic diagram illustrating a light propagation path distribution between the light incident and detection position and the probe region in the arrangement of FIG. 3.

In this case, a light propagation path distribution 18 from the light incident position $\gamma_s$ to the position $\gamma_p$ of the probe region 6 is substantially the same as a light propagation path distribution 18 from the probe region 6 to the light detection position $\gamma_d$, as shown in FIG. 4. In other words, the incident light propagation area of light emitted from the light source 1 overlaps the detection light propagation area of modulation light detected by the photodetector 8, so that those areas are regarded as identical to each other. Accordingly, the light going and returning in the same propagation path distribution is detected as a modulation signal $I_{AC}$. The former transfer function $\Psi(\gamma_s, \gamma_p)$ is therefore equal to the latter transfer function $\Psi(\gamma_p, \gamma_d)$ ($\Psi(\gamma_s, \gamma_p) = \Psi(\gamma_p, \gamma_d)$). In addition, the transfer function $\Psi(\gamma)$ is reversible. Thus, Expression 4 is obtained.

The light transfer function $\Psi$ from the light incident position $\gamma_s$ to the position $\gamma_p$ of the probe region 6 is therefore expressed based on Expression (4) by the following expression.

$$\Psi(r_s, r_p) = \sqrt{\frac{I_{AC}(r_p)}{S_O \eta}} \quad (5)$$

This transfer function reflects optical characteristics of tissues from the light incident position $\gamma_s$ up to the local probe region 6 inside the specimen 7.

As described above, it is preferable to calculate the light intensity $I_{AC}(\gamma_p)$ of modulated light in the local region using the relational expression (4) obtained on the condition that the incident light path is identical to the detection light path. When the incident light path and the detection light path are not regarded as identical to each other, the modulation signal in the AOT measurement reflects not only the optical characteristics of tissues in the incident light path but also those in the detection light path inside the specimen. On the other hand, in order to obtain an absorption characteristic in the probe region 6 using an acoustic signal obtained in the PAT measurement, the attenuation rate of light propagated in the incident light path, namely, the intensity of incident light which is affected by the optical characteristics of tissues in the incident light path in the specimen 7 and then reaches the probe region 6 is needed. In this instance, as will be described later, under the condition (first condition) that the incident light path and the detection light path are regarded as identical to each other, a target probe region 6 at a certain position may be subjected to the AOT measurement once. Under the condition (second condition) that the above-described paths are not regarded as identical to each other, however, the probe region 6 has to be subjected to the AOT measurement multiple times, a distribution of optical characteristics of tissues in the incident light path in the specimen 7 has to be estimated, and the light intensity in the probe region 6 has to be calculated. Accordingly, the light intensity can be calculated with high accuracy on the first condition, since it is more efficient because the number of AOT measurements is less than that on the second condition and the calculation is not affected by an error in the estimation of the distribution of optical characteristics on the second condition.

Detection of an acoustic signal in the PAT measurement from the same probe region 6 as that in the AOT measurement will now be described. When $S'_O$ denotes the intensity of incident light in the PAT measurement, the light intensity $\Psi(\gamma_p)$ in the probe region 6 is expressed using Expression (5) as follows.

$$\Psi(\gamma_p) = S'_O \Psi(\gamma_s, \gamma_p) \quad (6)$$

Using Expressions (1), (5), and (6), the sound pressure $P(\gamma_p)$ of a generated acoustic wave is expressed by the following expression.

$$P(r_p) = \Gamma \mu_a(r_p) S'_0 \Psi(r_s, r_p) = \Gamma \mu_a(r_p) S'_0 \sqrt{\frac{I_{AC}(r_p)}{S_o \eta}} \quad (7)$$

Accordingly, an absorption coefficient $\mu_a(\gamma_p)$ in the probe region 6 is expressed by the following expression.

$$\mu_a(r_p) = \frac{1}{\Gamma S'_0} \sqrt{\frac{S_o \eta}{I_{Ac}(r_p)}} P(r_p) \quad (8)$$

So long as the sound pressure or frequency of an ultrasonic wave applied in the AOT measurement is constant, a modulation efficiency η depends on the refractive index, absorption coefficient, and scattering coefficient of the probe region 6 and an anisotropic scattering parameter. In typical biological soft tissue, however, when a probe region has a sufficient small volume (of several cubic millimeters, for example), a change in modulation efficiency η is small. Accordingly, the change is regarded as substantially constant. So long as light with a constant intensity is applied to biological tissue at any time in each of the AOT measurement and the PAT measurement and a Gruneisen coefficient Γ is substantially constant independent of position, the following relational expression is obtained from Expression (8).

$$\mu_a(r_p) = C \frac{P(r_p)}{\sqrt{I_{AC}(r_p)}} \quad (9)$$

The modulation signal $I_{AC}(\gamma_p)$ indicating the light intensity and an acoustic wave $P(\gamma_p)$ are measured in the same probe region 6 in the AOT measurement and the PAT measurement, so that an absorption characteristic $\mu_a(\gamma_p)$ of the probe region $\gamma_p$ can be obtained using Expression (9).

The probe regions $\gamma_p$ are three-dimensionally scanned and are subjected to measurements, so that a relative internal distribution of absorption coefficients in the specimen 7 can be visualized. If respective parameters as constants in Expression (9) are previously obtained by calibration, an absorption coefficient can also be calculated.

To obtain an absorption coefficient $\mu_a$ from an acoustic signal in the PAT measurement, it is necessary to estimate a light intensity at a position where the acoustic wave has been generated. As a feature of the present invention, this estimation is performed using a modulation signal obtained in the AOT measurement. According to the present embodiment, it is preferable to perform the AOT measurement under the condition that the incidence optical fiber 2 and the detection optical fiber 3 are arranged so that the positions of those optical fibers are regarded as substantially the same relative to the probe region 6. In this case, a light transfer function according to the position of the probe region 6 can be obtained from a modulation signal in the AOT measurement. Since the AOT measurement and the PAT measurement are performed on the same probe region, a light intensity for conditions of the PAT measurement can be estimated using Expression (6).

As described above, to calculate the absorption coefficient of the local region on the basis of the acoustic signal obtained in the PAT measurement using Expression (1), the light intensity is calculated on the basis of the modulation signal obtained in the AOT measurement using Expression (6). Finally, the absorption coefficient can be calculated as expressed by Expression (9).

The above-described related-art method of estimating a light intensity using an average light attenuation coefficient is accurately applied to an ideal homogeneous medium. On the other hand, the analysis method according to the present invention is applicable to any specimen 7 irrespective of whether the specimen 7 includes homogenous or heterogeneous tissue. If the specimen 7 is heterogeneous, the modulation signal $I_{AC}$ of light which has gone and returned in the heterogeneous medium is obtained, the transfer function Ψ reflecting the heterogeneity is obtained using the signal $I_{AC}$, and the light intensity is estimated using the transfer function. In other words, an absorption coefficient is obtained in consideration of the heterogeneity of the medium.

Figure 5:
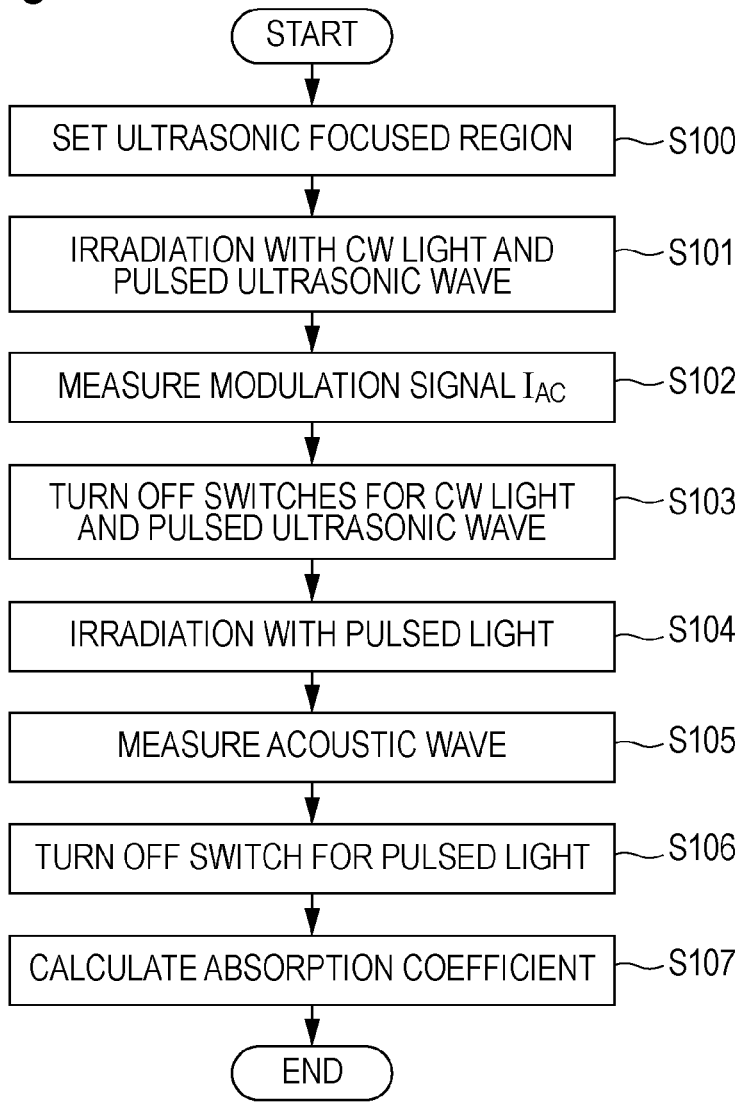
FIG. 5 is a flowchart of a measuring process in the implementation of a biological information processing method according to the first embodiment.

FIG. 5 illustrates an exemplary flowchart of a measuring process in the implementation of the biological information processing method according to the present embodiment. In step S100, a probe region 6 is set. The AOT measurement is performed in the subsequent steps. In step S101, the probe region 6 is irradiated with CW light and is also irradiated with a pulsed ultrasonic wave. In step S102, the photodetector 8 detects light modulated in the probe region 6. The signal extracting unit 10 in the signal processing device 9 selectively extracts only a signal of light modulated at the frequency of the ultrasonic wave to measure a modulation signal $I_{AC}$. The measured modulation signal is stored into the memory 13. At the completion of the AOT measurement, in step S103, a switch for the CW light and that for the pulsed ultrasonic wave are turned off.

Subsequently, the PAT measurement is performed. In step S104, the probe region 6 is irradiated with pulsed light. In step S105, the ultrasonic transducer 5 detects an acoustic signal generated in the probe region 6. As for setting for ultrasonic reception at that time, the probe region 6 is set in the same position as that set in the AOT measurement. The signal extracting unit 10 measures an acoustic wave in the probe region 6. The acoustic signal is stored into the memory 13. At the completion of the PAT measurement, in step S106, a switch for the pulsed light is turned off.

In step S107, the modulation signal obtained in the AOT measurement and the acoustic signal obtained in the PAT measurement are read out from the memory 13 to calculate an absorption coefficient $\mu_a(\gamma_p)$ of the probe region 6 using Expression (9).

Probe regions 6 inside the specimen 7 are scanned and each probe region 6 is sequentially subjected to the process in steps S100 to S107, thus obtaining an absorption distribution in the specimen 7. When all of sections inside the specimen 7 are scanned, an adsorption distribution in all of the sections inside the specimen 7 is obtained. The image generating unit 12 maps adsorption coefficients in association with the coordinates of the positions of the respective probe regions 6 to obtain a three-dimensional spatial distribution of absorption coefficients and generates an image of the distribution. The display device 14 displays the generated image.

Furthermore, the above-described process may be performed using a plurality of desired wavelengths of the light source 1 to obtain metabolic information, such as a proportion of elements, e.g., oxyhemoglobin, deoxyhemoglobin, water, fat, and collagen and an oxygen saturation index, of the specimen 7 through the arithmetic processing unit 11. Obtained functional information items are mapped in association with the coordinates of the positions of the respective probe regions 6 in a manner similar to the above-described process. The image generating unit 12 generates a three-dimensional tomogram on the basis of these information items and the display device 14 displays the tomogram.

In the flowchart of FIG. 5, the AOT measurement is performed and, after that, the PAT measurement is performed. This order may be reversed so that the PAT measurement is performed and, after that, the AOT measurement is performed.

Modifications of Device Configuration

Figure 6:
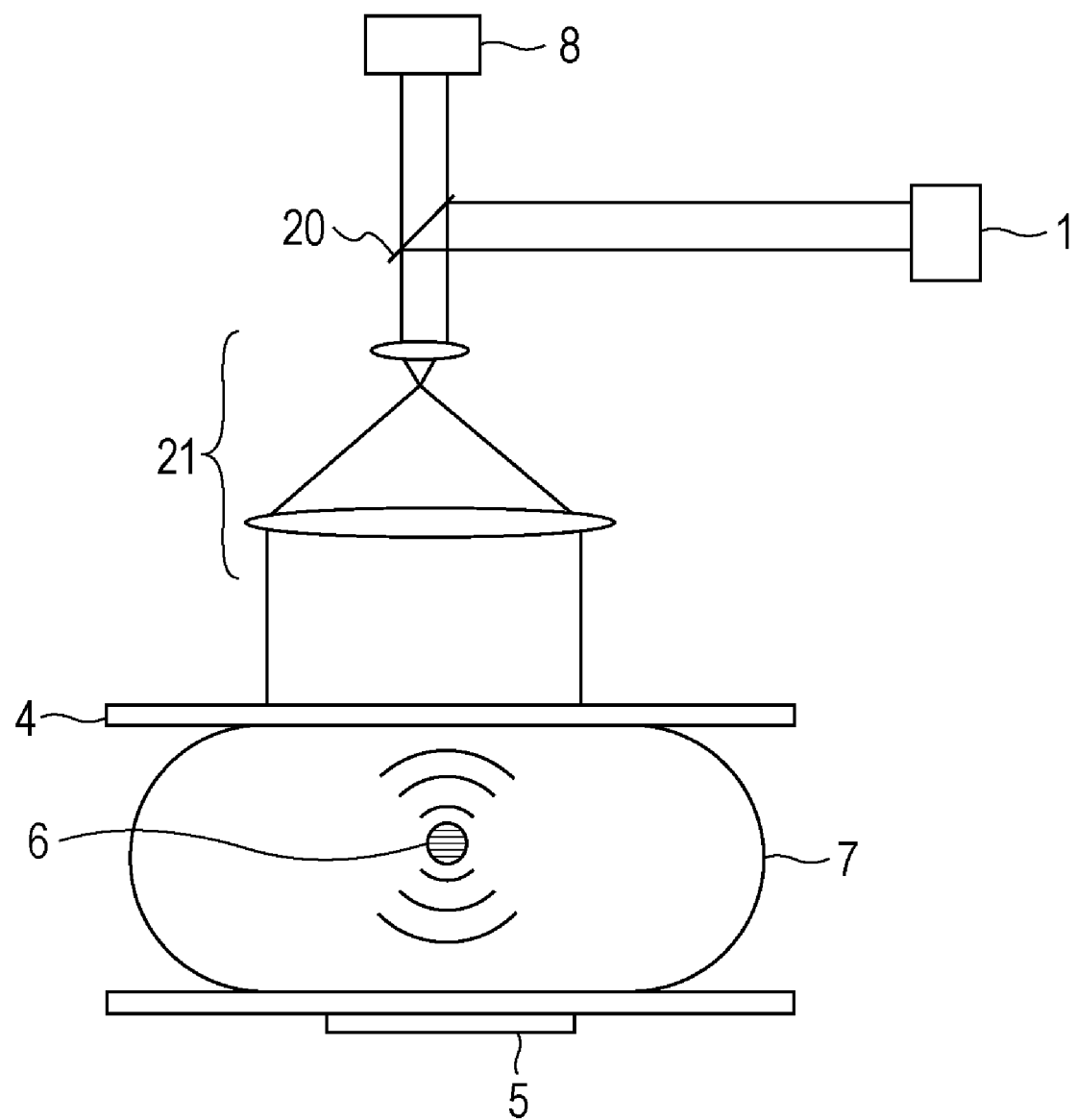
FIG. 6 is a schematic diagram illustrating another configuration of a measuring device in FIG. 1.
Figure 7:
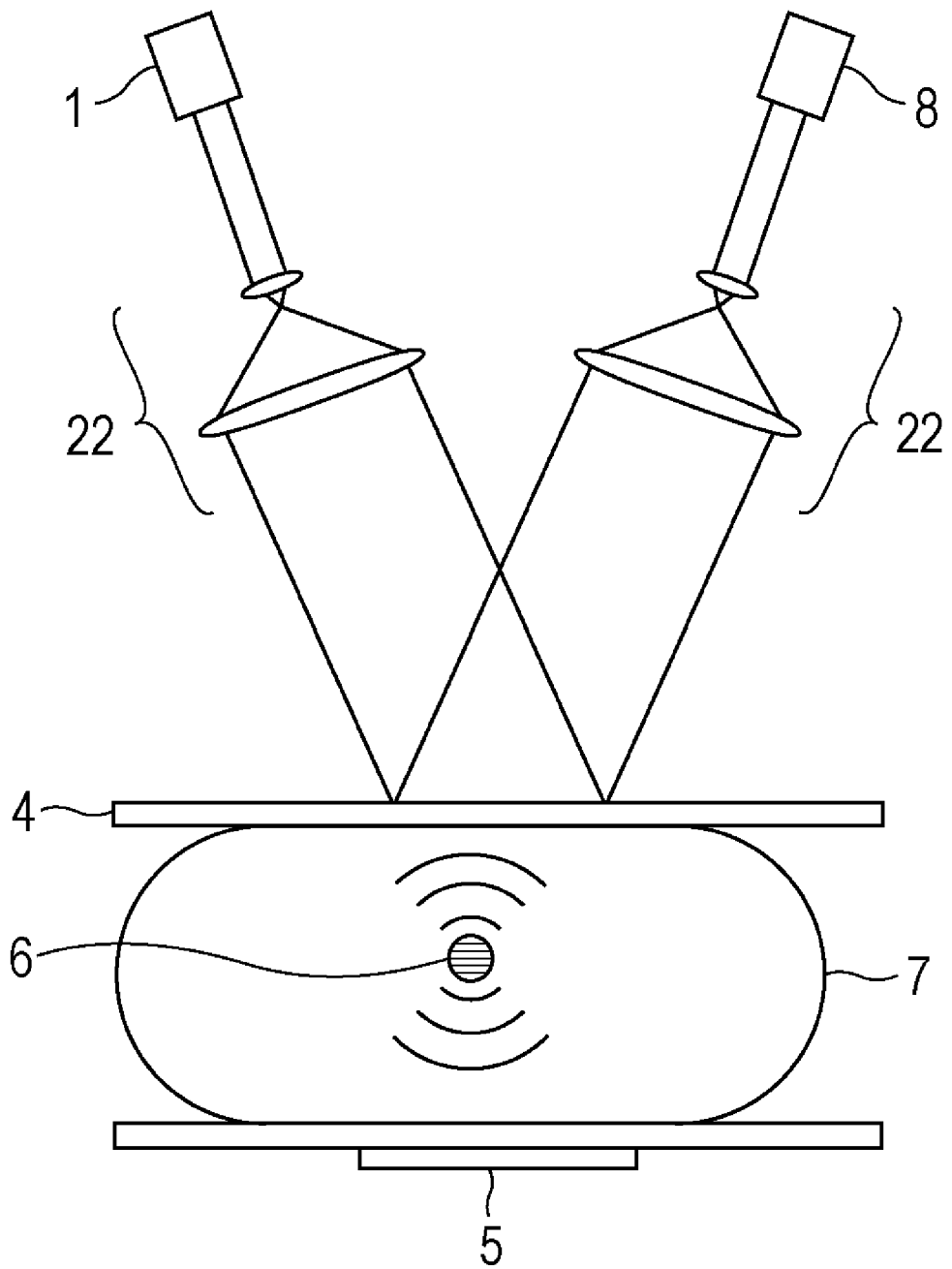
FIG. 7 is a schematic diagram illustrating another configuration of the measuring device in FIG. 1.
Figure 8:
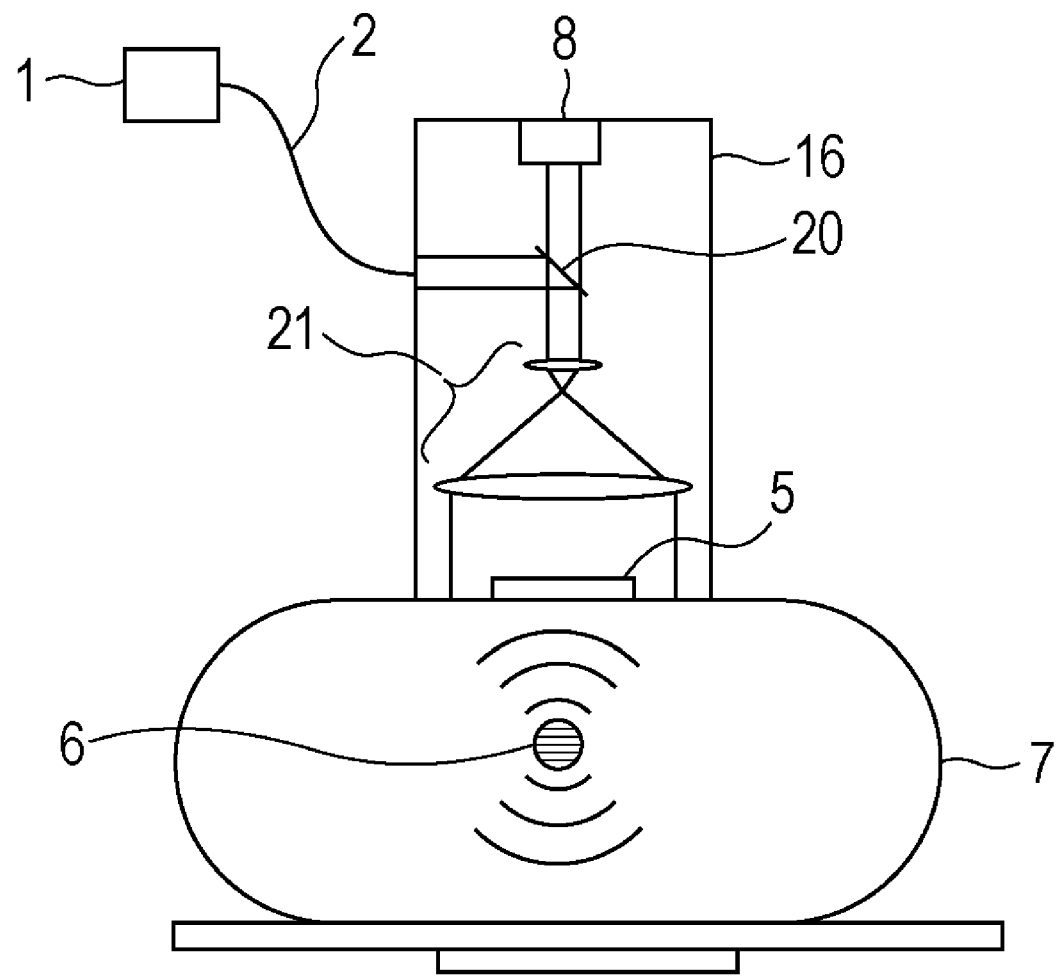
FIG. 8 is a schematic diagram illustrating another configuration of the measuring device in FIG. 1.

FIGS. 6 to 8 are schematic diagrams illustrating the configurations of measuring devices as modifications of the measuring device 19 in FIG. 1. In each configuration, the measuring device 19 includes no optical fibers. The devices, such as the signal processing device 9, other than the measuring device 19 have the same configuration as those in FIG. 1.

Referring to FIG. 6, a beam emitted from the light source 1 is reflected by a beam splitter 20. The reflected beam passes through an irradiation/detection optical system 21. A relatively large area of the specimen 7 is irradiated with the resultant light. Upon detection in the AOT measurement, light is focused through the same irradiation/detection optical system 21 as that upon irradiation and the focused light passes through the beam splitter 20. The photodetector 8 detects signal light. Irradiation and detection are performed using the same optical system to provide the same light passing portion. Thus, geometrical conditions similar to those in FIG. 3 can be set.

The configuration of FIG. 7 may be used when the probe region 6 is located sufficiently deep in the specimen 7 so that diffusion approximation is established. The same optical system is used for both of irradiation and detection. The same light passing portion relative to the specimen 7 is set for both of irradiation and detection. Light incident on the specimen 7 at an angle is isotropically scattered while being repeatedly scattered inside the specimen 7. Back-scattered light is also isotropically scattered. Light outgoing from the specimen 7 is detected. With this configuration, a light irradiation area and a light detection area can be set to substantially the same area.

The configuration of FIG. 8 may be used. Although this configuration is fundamentally the same as that of FIG. 6, measurement is performed while a measurement probe 16 is in contact with the specimen 7 as shown in FIG. 8. Inside the measurement probe 16, the photodetector 8, the ultrasonic transducer 5, the beam splitter 20, and the optical system 21 are received. The space between the measurement probe 16 and the specimen 7 is filled with a matching medium for acoustic impedance matching. In FIG. 8, a light irradiation area and a light detection area can also be set to substantially the same area.

As a method for AOT measurement, any of a method using a single sensor, such as a PMT, parallel detection using a multi-sensor, such as a CCD, hologram detection using a photorefractive element, and detection using spectral hole burning is available.

Second Embodiment

Figure 9:
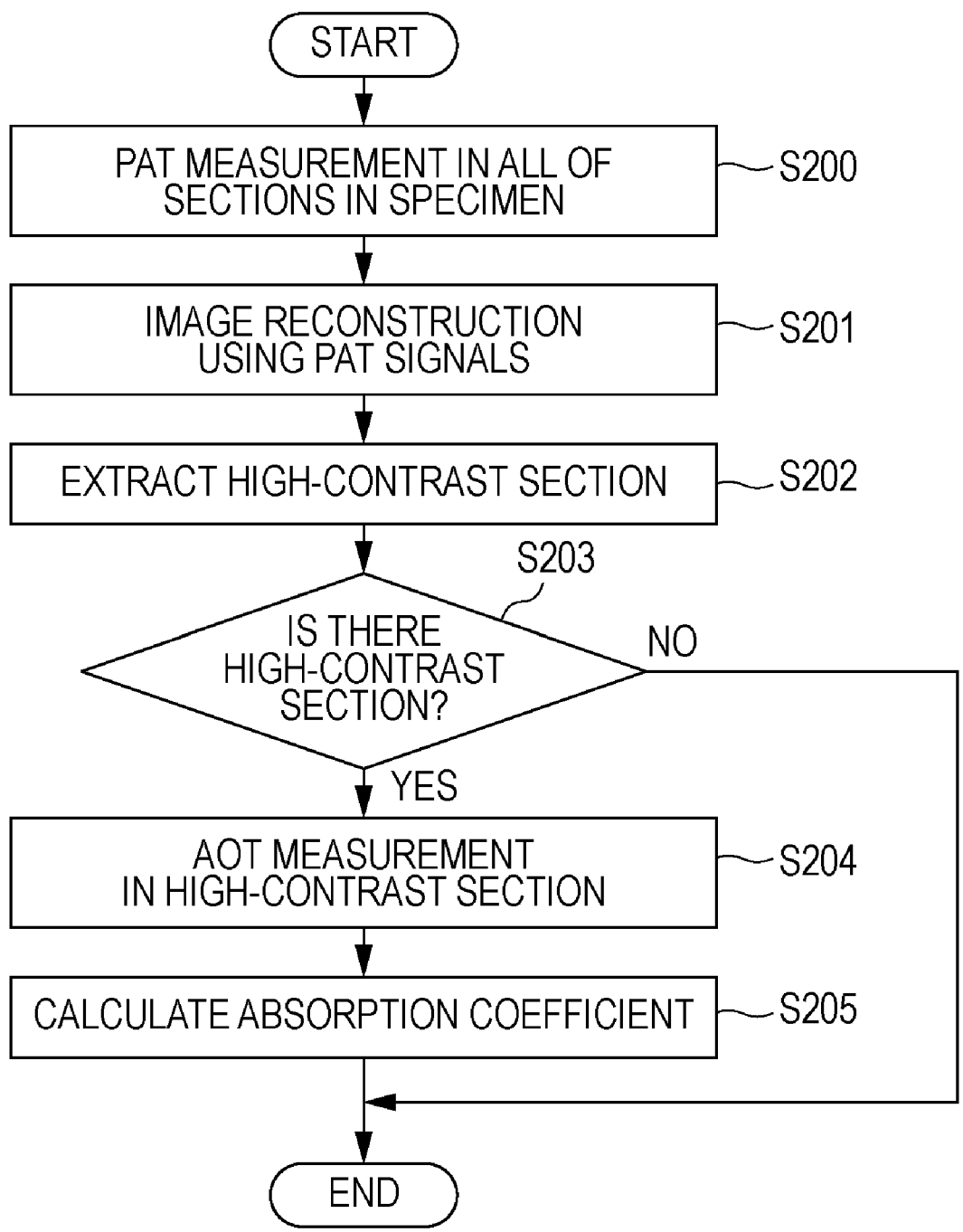
FIG. 9 is a flowchart illustrating a measuring process in the implementation of a biological information processing method according to a second embodiment.

A biological information method according to a second embodiment of the present invention will now be described. The configuration of an apparatus in this embodiment is the same as that of the apparatus in the first embodiment. FIG. 9 illustrates a flowchart of a measuring process in the present embodiment. In step S200, the PAT measurement is performed while the surface of one of the specimen fixing plates 4 is two-dimensionally scanned by the incidence optical fiber 2, thus obtaining PAT measurement values in all of sections in the specimen 7. At that time, it is preferable that measurement be performed at a plurality of wavelengths to obtain spectral information.

In step S201, image reconstruction is performed on the basis of signals obtained in step S201 using a well-known method disclosed in, for example, Non-patent Document 1, thus obtaining a distribution of sound pressures inside the specimen 7. At that time, the attenuation of an ultrasonic wave upon propagating the medium and a system error caused by the measuring device 19 or the signal processing device 9 are removed from the results of PAT measurements and information for reconstruction of the distribution of sound pressures generated upon pulsed light irradiation is obtained.

In step S202, a section (high-contrast section) with higher contrast than those of surrounding sections is extracted from the reconstructed image. In this case, a threshold value is previously set. A determination is made on each of the measured sections as to whether the contrast of the target section is higher than the threshold value as an average background signal value.

If there is no high-contrast section whose contrast exceeds the predetermined threshold value in step S203, the process is terminated. Whereas, if there is at least one high-contrast section, data indicating the coordinates of the position of this section is stored into the memory 13. The process proceeds to step S204.

In step S204, the probe region 6 for the ultrasonic transducer 5 is set in accordance with the coordinates of the position of the high-contrast section and the AOT measurement is performed. The AOT measurement is performed on each of the high-contrast sections extracted in step S202. Furthermore, it is preferable to similarly perform the AOT measurement in any of the positions of background sections other than the high-contrast sections.

In step S205, necessary information items related to each high-contrast section, for example, the result of PAT measurement and information after reconstruction, are extracted from the memory 13 and a sound pressure value is converted into an absorption coefficient on the basis of the information items using Expression (9). Similarly, an absorption coefficient related to the background section is obtained. After that, information regarding a distribution of absorption coefficients is obtained and the distribution is imaged. The display device 14 displays the obtained image. Consequently, the absorption coefficient of each high-contrast section can be evaluated relative to the absorption coefficient of the background section.

Furthermore, it is preferable to obtain metabolic information, such as a proportion of elements, e.g., oxyhemoglobin, deoxyhemoglobin, water, fat, and collagen, and an oxygen saturation index, from the absorption coefficient image through the arithmetic processing unit 11. These functional information items are imaged and the resultant image is displayed in the display device 14.

In this embodiment, PAT measurement is performed on each section inside biological tissue and at least one section where an acoustic signal has been obtained with higher contrast than a predetermined threshold value is specified. As described above, a section where biological tissue may be abnormal is specified on the basis of the PAT measurements and the AOT measurement is performed on the section, so that measurement time can be reduced and necessary information can be efficiently obtained. Although the AOT measurement and the PAT measurement are successively performed on the probe region 6 in the first embodiment, the AOT measurement is performed independent of the PAT measurement in this embodiment.

As for the configuration of the measuring device, any of the configurations illustrated in FIGS. 6 to 8 may be used.

Third Embodiment

A biological information processing method according to a third embodiment of the present invention will now be described. The configuration of an apparatus in the present embodiment is the same as that in the first embodiment. In the first embodiment, the incidence optical fiber 2 and the detection optical fiber 3 are arranged so that their positions are regarded as substantially the same position relative to the probe region 6. In the present embodiment, the optical fibers are arranged at any distance therebetween. Typically, it is preferable to arrange the optical fibers at a distance of several centimeters. In the present embodiment, a method of calculating a light intensity in a local region using the AOT is different from that in the first embodiment.

Figure 10:
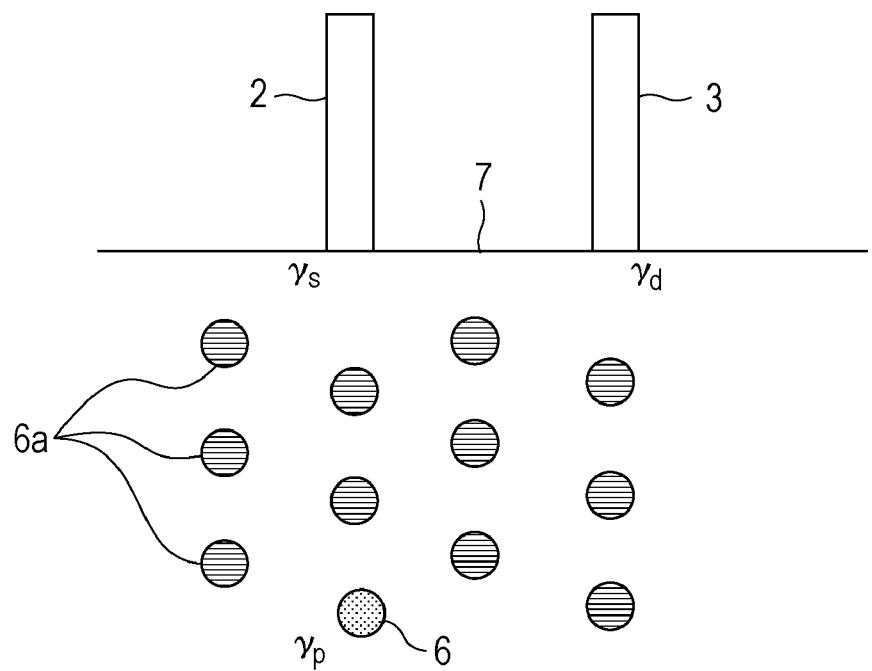
FIG. 10 is a schematic diagram illustrating the positional relation among a light incident position, a light detection position, and a plurality of probe regions in a third embodiment.

Referring to FIG. 10, modulated-light measurement regions 6a in each of which an AOT signal along is acquired are arranged below the surface of the specimen 7 such that the respective regions 6a are located relative to the probe region 6 where an absorption coefficient is to be obtained and modulated light in each region 6a is measured.

A light attenuation coefficient $\mu_{eff}(\gamma)$ in the position $\gamma$ of each modulated-light measurement region 6a is estimated using the AOT in the manner disclosed in U.S. Pat. No. 6,957,096 as follows.

Propagation of multiple scattered light is expressed using the attenuation coefficient $\mu_{eff}(\gamma)$ and a diffusion equation as follows.

$$(\nabla^2 - \mu^2_{eff}(\gamma))U(\gamma) = S(\gamma) \quad (10)$$

where $U(\gamma)$ denotes the intensity of scattered light and $S(\gamma)$ denotes the intensity of light emitted from the light source. A distribution of modulated-light intensities is expressed using Expression (3).

According to U.S. Pat. No. 6,957,096, the following relational expression is derived using Expression (3) and Expression (10).

$$\mu^2_{eff}(r) = \frac{2}{1+\cos\theta} \frac{\nabla^2 \sqrt{I_{AC}(r)}}{\sqrt{I_{AC}(r)}} \quad (11)$$

In Expression (11), θ denotes an angle shown in FIG. 2, the angle being formed by a vector extending from the position $\gamma_p$ of the probe region 6 to the light incident position $\gamma_s$ and another vector extending from the position $\gamma_p$ of the probe region 6 to the light detection position $\gamma_d$.

Using Expression (11), the attenuation coefficient $\mu_{eff}(\gamma)$ can be calculated using the modulation signal obtained in the AOT measurement. Referring to FIG. 10, the attenuation coefficients $\mu_{eff}(\gamma)$ of the respective modulated-light measurement regions 6a located between the surface of the specimen 7 and the probe region 6 are sequentially calculated using Expression (11). In this case, the attenuation coefficient $\mu_{eff}(\gamma)$ obtained in a modulated-light measurement region 6a closer to the surface may be reflected in Expression (10), serving as the diffusion equation, to obtain the attenuation coefficient $\mu_{eff}(\gamma)$ in a deeper region.

Regions other than the modulated-light measurement regions 6a are spatially interpolated using the attenuation coefficients $\mu_{eff}(\gamma)$ spatially discretely obtained, as shown in FIG. 10, to obtain a distribution of attenuation coefficients $\mu_{eff}(\gamma)$. The obtained spatial distribution of attenuation coefficients $\mu_{eff}(\gamma)$ is processed using, for example, the Lambert-Beer Law and the diffusion equation, alternatively, the Monte Carlo simulation, thus obtaining the light intensity $\Phi(\gamma_p)$ in the probe region 6.

The light intensity $\Phi(\gamma_p)$ obtained as described above is substituted into Expression (1). Accordingly, an absorption coefficient $\mu_a(\gamma_p)$ in the probe region 6 can be obtained on the basis of an acoustic signal generated in the probe region 6 in the PAT measurement using Expression (1).

As described above, in the present embodiment, the AOT measurement is performed in each of a plurality of positions inside biological tissue. A spatial distribution of light attenuation coefficients in regions located between a light incident position and a probe region is calculated using modulation signals obtained in the AOT measurements. A light intensity in the probe region is calculated using the spatial distribution. An absorption coefficient is obtained using the light intensity, an acoustic signal in the PAT measurement, and Expression (1). In the present embodiment, an absorption characteristic value in the probe region in the PAT measurement can be obtained using modulation signals obtained in the AOT measurements without being restricted by the position of a probe as in the first embodiment.

In this embodiment, after the PAT measurement is performed in all of sections in the specimen 7 and image reconstruction is performed as described in the second embodiment, the method according to the present embodiment may be applied to a high-contrast section. In this case, the specimen 7 is segmented into sections having the same size as that of the probe region and an attenuation coefficient $\mu_{eff}(\gamma)$ in each section is estimated on the basis of the obtained attenuation coefficients $\mu_{eff}(\gamma)$ in the positions γ of the respective modulated-light measurement regions 6a. Inverse problem estimation as disclosed in Non-patent Document 1 is implemented on an AOT model disclosed in U.S. Pat. No. 5,840,023, thus obtaining a more detailed spatial distribution of attenuation coefficients $\mu_{eff}(\gamma)$.

Alternatively, the AOT measurement and the PAT measurement may be performed in each section in the specimen 7 in the same way as in the first embodiment. Using Expression (11), attenuation coefficients $\mu_{eff}(\gamma)$ in all of the probe regions 6 in the respective sections in the specimen 7 may be obtained in the AOT measurement. A light intensity $\Phi(\gamma_p)$ in each probe region 6 may be calculated on the basis of a spatial distribution of the obtained attenuation coefficients $\mu_{eff}(\gamma)$ using the diffusion equation. A sound pressure obtained from each probe region in the PAT measurement may be converted into an absorption coefficient using the light intensity $\Phi(\gamma_p)$. The converted absorption coefficients may be imaged.

In this embodiment, if the specimen 7 includes heterogeneous tissue, a spatial distribution of attenuation coefficients $\mu_{eff}(\gamma)$ is obtained by the AOT measurement, thus calculating a local light intensity in each probe region 6. An absorption coefficient can be obtained from a PAT signal with high accuracy.

Fourth Embodiment

A biological information processing method according to a fourth embodiment of the present invention will now be described. The configuration of an apparatus in the present embodiment is the same as that in the first embodiment. Prior to the AOT measurement or the PAT measurement, a pulsed ultrasonic wave is transmitted from the ultrasonic transducer 5 and an ultrasonic echo, serving as a reflected wave, is received by the ultrasonic transducer 5. The measurement is performed while the direction in which the pulsed ultrasonic wave is transmitted is changed relative to the specimen 7, thus obtaining structural data regarding the inside of the specimen 7. The data is stored into the memory 13.

In the arithmetic processing unit 11, the structural data regarding the inside of the specimen 7 obtained by the ultrasonic echo measurement is read out from the memory 13, the specimen 7 is segmented into sections using structural features, and structural information regarding the sections is stored into the memory 13. The structural features specify a section in which an echo signal obtained by the ultrasonic echo measurement has been obtained with higher contrast than a previously set threshold value. As described above, a section having a tissue structural feature is extracted using an ultrasonic echo signal.

Figure 11:
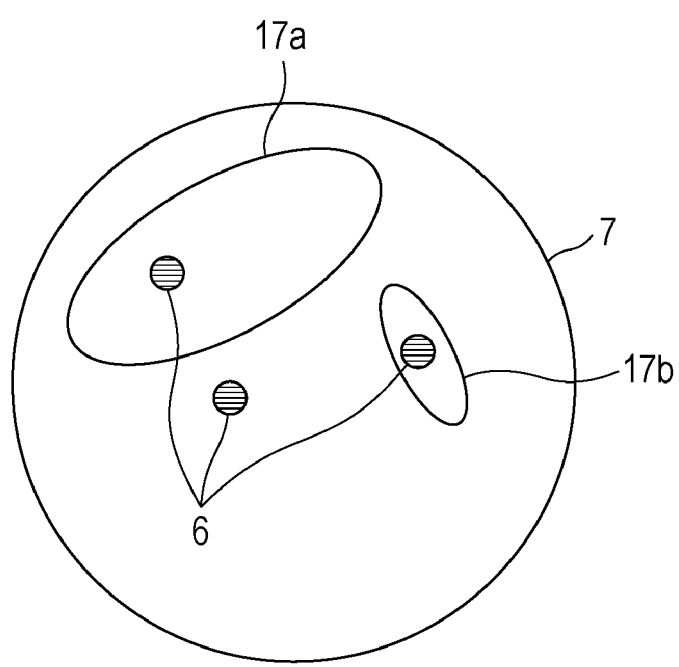
FIG. 11 is a schematic diagram illustrating the positional relation among segmented sections and probe regions inside biological tissue in a fourth embodiment.

In the AOT measurement, the above-described structural information regarding the sections is used. For example, as shown in FIG. 11, the specimen 7 is segmented into sections, e.g., a section A (17a), a section B (17b), and other sections on the basis of the structural information regarding the sections. Since the respective sections differ from one another in terms of tissues, optical characteristics, such as absorption coefficients and scattering coefficients, in the respective sections also differ from one another. In the AOT measurement, therefore, an attenuation coefficient $\mu_{eff}(\gamma)$ in each section is obtained using, for example, the method according to the third embodiment.

Assuming that each section is substantially homogeneous optically and therefore has a constant attenuation coefficient $\mu_{eff}(\gamma)$, a light intensity $\Phi(\gamma_p)$ in each probe region 6 is calculated on the basis of a distribution of the attenuation coefficients. After that, an absorption coefficient $\mu_a(\gamma_p)$ in the region is obtained on the basis of an acoustic signal in the PAT measurement.

Alternatively, an internal distribution of the attenuation coefficients $\mu_{eff}(\gamma)$ in the specimen 7 may be reconstructed from a plurality of AOT measurements by solving inverse problem using the structural data, as disclosed in A. P. Gibson et al., "Recent advances in diffuse optical imaging", Phys. Med. Biol., 50 (2005), R1-R43. In this case, a light intensity in a probe region is calculated using a non-uniform spatial distribution of attenuation coefficients, thus obtaining an absorption characteristic value in the probe region in the PAT measurement.

In the present embodiment, a specimen is divided into a plurality of sections on the basis of ultrasonic echoes in advance. A light intensity in a local region is calculated using a spatial distribution of light attenuation coefficients obtained in the respective sections. Consequently, an optically heterogeneous section is efficiently extracted using structural information and the AOT measurement can be selectively performed, so that measurement time can be reduced.

Other Embodiments

The present invention can also be achieved by performing the following process: Software (program) for implementing the functions of the above-described embodiments is supplied to a system or apparatus through a network or various storage media. A computer (or CPU or MPU) of the system or apparatus is allowed to read out and execute the program.

In this case, the program code itself read out from the storage medium implements the functions of the foregoing embodiments. In other words, aspects of the present invention include the program code and the storage medium storing the program code.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2008-258570 filed Oct. 3, 2008, which is hereby incorporated by reference herein in its entirety.

What is claimed is:

1. An information processing apparatus comprising:
an ultrasonic wave transmitting unit configured to apply a focused ultrasonic wave to a local region of a specimen;
a photodetecting unit configured to detect modulated light generated by modulating light incident in the local region of the specimen with the ultrasonic wave, and to output a modulation signal;
an acoustic wave detecting unit configured to detect an acoustic wave emitted from the local region at a time when the local region absorbs the light, and to output an acoustic signal; and
an arithmetic unit configured to calculate a light intensity in the local region based on the modulation signal, and to calculate an absorption characteristic in the local region based on the acoustic signal and the light intensity in the local region.

2. The apparatus according to claim 1, wherein the ultrasonic wave transmitting unit and the acoustic wave detecting unit are realized by an elastic wave transducer.

3. The apparatus according to claim 1, wherein an incidence optical fiber and a detection optical fiber are arranged so that an incident light propagation area, where the light propagates to the local region through the specimen, overlaps a detection light propagation area where the modulated light propagates from the local region to the photodetecting unit through the specimen.

4. The apparatus according to claim 3, wherein the incidence optical fiber and the detection optical fiber are arranged so that the incident light propagation area and the detection light propagation area are regarded as identical to each other, and the arithmetic unit calculates the light intensity in the local region using a relational expression obtained on the condition that the incident light propagation area is identical to the detection light propagation area.

5. The apparatus according to claim 1, further comprising a light source configured to generate the light.

6. A method of processing specimen information, comprising the steps of:
- irradiating a local region of a specimen with a focused ultrasonic wave;
- detecting modulated light generated by modulating light incident in the local region with the ultrasonic wave;
- outputting a modulation signal by detecting the modulated light;
- detecting an acoustic wave emitted from the local region by irradiating the local region with the light;
- outputting an acoustic signal by detecting the acoustic wave;
- calculating a light intensity in the local region based on the modulation signal; and
- calculating an absorption characteristic in the local region using the acoustic signal and the light intensity in the local region.

7. The method according to claim 6, wherein the irradiating of the local region with the light and the detecting of the modulated light are performed so that an incident light propagation area, where the light propagates to the local region through the specimen, overlaps a detection light propagation area where the modulated light to be detected propagates from the local region through the specimen.

8. The method according to claim 7, wherein
the irradiating of the local region with the light and the detecting of the modulated light are performed so that the incident light propagation area and the detection light propagation area are regarded as identical to each other, and
the light intensity in the local region is calculated using a relational expression obtained on the condition that the incident light propagation area is identical to the detection light propagation area.

9. The method according to claim 6, wherein
in the step of detecting the acoustic wave, the acoustic wave is detected in any local region in the specimen,
the method further includes the step of specifying a section in which the acoustic signal is obtained with higher contrast than a predetermined threshold value in the specimen, and
the local region is set in the specified section and the modulated light is detected.

10. The method according to claim 6, wherein
the step of detecting the modulated light includes the sub-steps:
detecting modulated light from each of positions inside the specimen to calculate a spatial distribution of light attenuation coefficients inside the specimen; and
calculating the light intensity in the local region using the spatial distribution.

11. The method according to claim 10, further comprising the step of:
segmenting the specimen into a plurality of sections on the basis of ultrasonic echoes obtained by applying the ultrasonic wave to the specimen, wherein
the light intensity in the local region is calculated using the spatial distribution of light attenuation coefficients calculated in the respective sections.

12. The method according to claim 6, wherein the absorption characteristic obtained in the local region is associated with the coordinates of the position of the local region to form a three-dimensional tomogram relating to the absorption characteristics in the specimen.

13. A non-transitory computer-readable recording medium that records a program allowing a computer to execute the method according to claim 6.

* * * * *